United States Patent
Wise

(10) Patent No.: US 8,128,971 B1
(45) Date of Patent: Mar. 6, 2012

(54) METHOD AND FORMULA FOR TREATING CELIAC DISEASE

(76) Inventor: Jack Wesley Wise, Tulsa, OK (US)

( * ) Notice: Subject to any disclaimer, the term of this patent is extended or adjusted under 35 U.S.C. 154(b) by 36 days.

(21) Appl. No.: 12/815,471

(22) Filed: Jun. 15, 2010

(51) Int. Cl.
*A61K 36/00* (2006.01)
*A61K 8/67* (2006.01)

(52) U.S. Cl. .......................................... 424/725; 424/73

(58) Field of Classification Search ........................ None
See application file for complete search history.

(56) References Cited

OTHER PUBLICATIONS wikipedia.org. Retrieved from the internet. <http://web.archive.org/web/20081219083451/http://en.wikipedia.org/wiki/Dyspepsia>. Retrieved on Oct. 21, 2011. Web archive date. Aug. 19, 2008. 3 pages.*
mercola.com. Retrieved from the internet. <http://web.archive.org/web/20080509032308/http://articles.mercola.com/sites/articles/archive/2002/10/12/gerd.aspx>. Retrieved on Oct. 21, 2011. Web archive date May 9, 2008. 3 pages.*
wikipedia.org. Retrieved from the internet on Oct. 21, 2011. <http://en.wikipedia.org/wiki/Nucleic_acid>. 4 pages.*
Viable-herbal.com. Retrieved from the internet. Retrieved on Oct. 21, 2011. Web archive date Jan. 24, 2000. <http://web.archive.org/web/20000124113842/http://viable-herbal.com/herbology1/herbs42.htm>. 3 pages.*
theodora.com. Retrieved from the internet. Retrieved on Oct. 22, 2011. Web archive date Feb. 2, 2008. <http://web.archive.org/web/20080209132845/http://www.theodora.com/drugs/ambrotose_capsules_ambrotose_powder_ambrotose_with_lecithin_capsules_mannatech.html>. 2 pages.*
thehealthierlife.co. Nature's Lining: New Natural Indigestion Remedy Launched in UK. Retrieved from the internet on Oct. 21, 2011. <http://www.thehealthierlife.co.uk/natural-health-articles/digestive-problems/natures-lining-natural-indigestion-remedy-00132.html>. Jan. 4, 2004. 3 pages.*
Rose. Melatonin and sleep qualities in healthy adults: Pharmacological and expectancy effects. The Journal of General Psychology. Oct. 2001. vol. 128, Iss. 4. p. 401, 21 pages. (pp. 1-12 from ProQuest).*
healthmad.com. Retrieved from the internet. <http://healthmad.com/nutrition/10-benefits-of-aronia-berry/>. Jul. 10, 2008. Retrieved from the internet on Oct. 20, 2011. 10 pages.*
Daily Record. Sooth your spirits the natural way. Daily Record. Glaskow. Dec 15, 1999. p. 4. (2 pages from ProQuest).*
Anonymous. Homeopathic First Aid Kit: Solutions for Summer's :ittle Bummers. U.S. Newwire. Jul. 1, 2008. pp. 1-2 of ProQuest.*
Balch. Prescription for Natural Cures: A Self-care Guide for Treating Health. John Wiley and Sons. 2004. p. 347.*

\* cited by examiner

*Primary Examiner* — Melenie McCormick
(74) *Attorney, Agent, or Firm* — Molly D. McKay

(57) ABSTRACT

A homoeopathic formula and method for treating celiac disease. The formula includes the ingredients of L-Carnosine, Aronia Berry, Vitamin D3, Folic Acid, RNA, DNA, *Pulsitilla*, and *Lycopodium Clavatium* which are mixed with brown rice flour as an anti clumping agent prior to encapsulating the formula in standard gel caps. The preferred dosage for the treatment of celiac disease is to administer 6 capsules of the preferred formulation to the patient orally each day for 30 consecutive days.

3 Claims, No Drawings

METHOD AND FORMULA FOR TREATING CELIAC DISEASE

BACKGROUND OF THE INVENTION

1. Field of the Invention

The present invention is a formula for the treatment of celiac disease. The formula is preferably encapsulated in standard gel caps which are to be taken by mouth.

2. Description of the Related Art

Celiac disease is an inherited, autoimmune disease in which the lining of the small intestine is damaged from eating gluten and other proteins found in wheat, barley, rye, and possibly oats. The exact cause of celiac disease is unknown. The intestines are lined with projections called villi that absorb nutrients from the food which passes through the intestines. In celiac disease, these villi become flattened which affects their ability to absorb nutrients properly. When untreated, the disease can cause life-threatening complications. It is estimated that there may be as many a 1% of population that is affected by this disease. Women are more prone to have the disease than men, and the disease may present itself at any age in patients.

Currently there is no known cure for celiac disease. Treatment for this disease is limited to following a lifelong gluten-free diet which allows the intestinal villi to heal. Following a well-balanced, gluten-free diet is generally the only treatment that will allow the celiac to stay well.

The symptoms of celiac disease vary from person to person. Some common symptoms that may be experienced by celiacs include abdominal pain, distention, bloating, gas and indigestion, constipation or diarrhea, changes in appetite, lactose intolerance, nausea and vomiting, irregularity of stools, unexplained weight loss, anemia and breathlessness due to anemia, joint pain, bone disease, bruising easily, defects or discoloration of dental enamel, depression, fatigue, delayed growth in children, hair loss, hypoglycemia, irritability and behavioral changes, malnutrition, mouth ulcers, muscle cramps, nosebleeds, seizures, unexplained short stature, skin disorders, swelling, and vitamin or mineral deficiency.

One treatment for the symptoms of celiac disease is taking vitamin and mineral supplements to correct nutritional deficiencies resulting from the disease. Occasionally, corticosteroids (such as prednisone) may also be prescribed for short-term use to treat symptoms of the disease.

The present invention has been shown to be helpful in the treatment of celiac disease. In addition to celiac disease, the present invention may also be helpful in treating other genetic based diseases, such for example cystic fibrosis and cycle cell anemia.

SUMMARY OF THE INVENTION

The present invention is a homoeopathic formula and method for the treatment of celiac disease. The formula is preferably encapsulated in standard gel caps which are to be taken by mouth.

The formula consists of L-Carnosine, Aronia Berry, Vitamin D3, Folic Acid, RNA, DNA, *Pulsitilla*, and *Lycopodium Clavatium*. The formula is preferably mixed with brown rice flour as an anti-clumping agent and then encapsulated in standard gel caps. Specifically, the preferred amount of each ingredient is as follows:

1,500 mg. L-Carnosine
2,000 mg. concentrated formula Aronia Berry
10,000 i.u. Vitamin D3
5 mg. Folic Acid
200 mg. RNA
200 mg. DNA
20 mg. *Pulsitilla*
40 mg. *Lycopodium Clavatium*

The amount of the individual ingredients of this formula can be varied by approximately 25%, but the efficacy of the resulting formulation may be lessened.

The preferred dosage for the treatment of celiac disease is to administer 6 capsules of the preferred formulation to the patient orally each day for approximately 30 consecutive days.

Although the exact mechanism by which the formula works is not know, it is postulated that the formula stimulates regrowth of villi which are able to more efficiently absorb nutrients.

DETAILED DESCRIPTION OF THE PREFERRED EMBODIMENT

The present invention is a homoeopathic formula and method for the treatment of celiac disease. The formula is preferably encapsulated in standard gel caps which are to be taken by mouth.

The formula consists of L-Carnosine, Aronia Berry, Vitamin D3, Folic Acid, RNA, DNA, *Pulsitilla*, and *Lycopodium Clavatium*. The formula is preferably mixed with brown rice flour as an anti-clumping agent and then encapsulated in standard gel caps.

Specifically, the preferred amount of each ingredient is as follows:

1,500 mg. L-Carnosine
2,000 mg. concentrated formula Aronia Berry
10,000 i.u. Vitamin D3
5 mg. Folic Acid
200 mg. RNA
200 mg. DNA
20 mg. *Pulsitilla*
40 mg. *Lycopodium Clavatium*

Of the ingredients listed above only *Pulsitilla* and *Lycopodium Clavatium* are classified as homoeopathic ingredients and the remaining 6 ingredients are considered herbs, vitamins or other inert ingredients. As previously stated, all of the ingredients are mixed with brown rice flour as an anti clumping agent prior to encapsulating the formula in standard gel caps. The proportion of brown rice flour employed is not critical. The individual components of this formula can be varied by approximately 25%, but the efficacy of the resulting formulation may be lessened.

The preferred dosage for the treatment of celiac disease is to administer 6 capsules of the preferred formulation to the patient orally each day for approximately 30 consecutive days.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. A formulation for oral administration for the treatment of celiac disease comprising the following ingredients:

L-carnosine, aronia berry, vitamin D3, folic acid, RNA, DNA, *Pulsitilla* and *Lycopodium clavatium*, wherein the ingredients are within 25% of the following amounts: 1,500 mg L-carnosine, 2,000 mg aronia berry, 10,000 i.u. vitamin D3, 5 mg folic acid, 200 mg RNA, 200 mg DNA, 20 mg *Pulsitilla*, and 40 mg *Lycopodium clavatium*.

2. The formulation for oral administration for the treatment of celiac disease according to claim 1, further comprising the following ingredients:

brown rice flour employed as an anti-clumping agent and gel caps.

3. The formulation for oral administration for the treatment of celiac disease according to claim 1, wherein the aronia berry is concentrated.

* * * * *